US00PP25501P3

(12) United States Plant Patent

Tupy et al.

(10) Patent No.: US PP25,501 P3

(45) Date of Patent: May 5, 2015

(54) COLUMNAR APPLE TREE NAMED 'ROSALIE'

(50) Latin Name: ***Malus domestica* (Borkh.)**
Varietal Denomination: ROSALIE

(75) Inventors: Jaroslav Tupy, Praha (CZ); Otto Louda, Pencin u Liberce (CZ); Jan Zima, Turnov (CZ)

(73) Assignee: Institute of Experimental Botany AS CR, V.V.I (UEB), Prague (CZ)

( * ) Notice: Subject to any disclaimer, the term of this patent is extended or adjusted under 35 U.S.C. 154(b) by 317 days.

(21) Appl. No.: 13/507,482

(22) Filed: Jul. 3, 2012

(65) Prior Publication Data

US 2014/0013473 P1 Jan. 9, 2014

(51) Int. Cl.
*A01H 5/00* (2006.01)

(52) U.S. Cl.
USPC ..... Plt./175

(58) Field of Classification Search
USPC ..... Plt./175, 172, 161
See application file for complete search history.

*Primary Examiner* — Kent L Bell

(74) *Attorney, Agent, or Firm* — The Webb Law Firm

(57) ABSTRACT

A new and distinct *Malus domestica* (Borkh.) apple tree variety is provided which exhibits a columnar tree type, moderate growth vigor, and $V_f$-resistance against scab. The new variety yields late maturing and ornamental fruits. The fruit color is medium red and the fruit size is large relative to other ornamental apples.

5 Drawing Sheets

Botanical classification: *Malus domestica* (Borkh.).
Varietal denomination: 'ROSALIE'.

BACKGROUND OF THE INVENTION

The present invention comprises a new and distinct cultivar of ornamental apple tree botanically classified as *Malus domestica* (Borkh.) and known by the varietal name 'ROSALIE'. The new variety is the result of a cross between 'Aneta' (female parent, unpatented) and 'Maypole' (male parent, U.S. Plant Pat. No. 6,184). The cross resulting in 'ROSALIE' occurred in the Spring of 1994 at 310 meters above sea level with a mean annual temperature of 7.7° C. and a mean annual precipitation of 680 mm. The purpose of the breeding program was to develop varieties of a columnar tree type with a unique appearance and resistance to scab. The new variety was discovered in 2002, with the first fruiting and flowering of the original seedling in The Czech Republic. Subsequently, the new variety was asexually reproduced in The Czech Republic by budding/grafting on apple rootstocks in the Spring of 2003.

The new variety is similar to 'Aneta' in that it exhibits the presence of $V_f$-resistance against scab. However, the new variety differs from 'Aneta' as 'ROSALIE' has a columnar tree type, reddish-purple flower color, smaller fruit size, and red-colored fruit flesh. Further, the new variety is similar to 'Maypole' in its columnar tree type, compact growth habit, purple color of unopened flowers, reddish-purple opened flower color, prominent petal veins, red fruit skin color, and red colored fruit flesh. However, the new variety is different from 'Maypole' as its petal shape is ovate instead of broadly elliptic, its petal position is overlapping instead of touching, and its fruit form is broadly globose conical versus globose conical. Further, the new variety has a larger fruit size, shorter fruit stalk, exhibits the presence of $V_f$-resistance against scab, and longer fruit persistence than 'Maypole'. The new variety is also similar to 'Redspring' (unpatented) in columnar apple tree type, red fruit skin color, and $V_f$-resistance against scab.

However, 'Redspring' produces dessert apples, while the apples of 'ROSALIE' are only for ornamental use. The following characteristics also distinguish the new variety from other varieties known to the breeders:

- Late fruit ripening, ornamental, diploid variety;
- Columnar tree type;
- Trees exhibit medium vigor;
- The growth habit is compact with very short internodes;
- Single flower type with a shallow cup form;
- Unopened and opened flowers are reddish-purple;
- Large fruit size relative to other ornamental apples;
- Broadly globose-conical fruit shape;
- Medium red fruit color;
- Fruit flesh color is predominantly red with some white present;
- Long fruit persistence; and
- $V_f$-resistance against scab.

The new variety has been trial and field tested and has been found to retain its distinctive characteristics and remain true to type through successive asexual propagations.

DESCRIPTION OF THE DRAWINGS

The accompanying photographic drawings illustrate the new cultivar, with the color being as nearly true as is possible with color illustrations of this type. It should be noted that colors may vary with growing conditions and time of year.

DESCRIPTION OF THE PLANT

Figure 1:
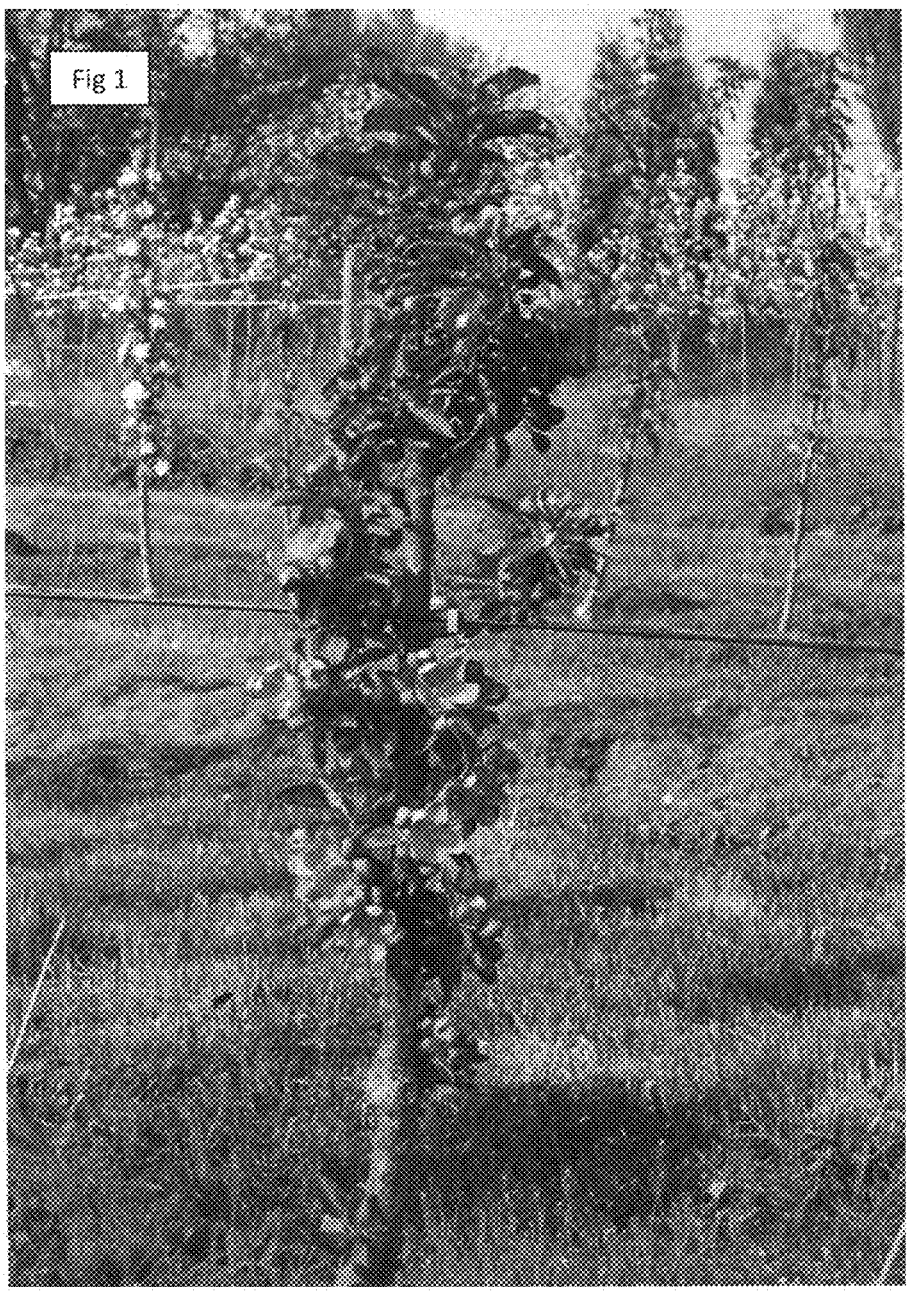
FIG. 1 is a photograph of a tree of the new variety grafted on MM 106 rootstock, showing canopy form at blossoming time.
Figure 2:
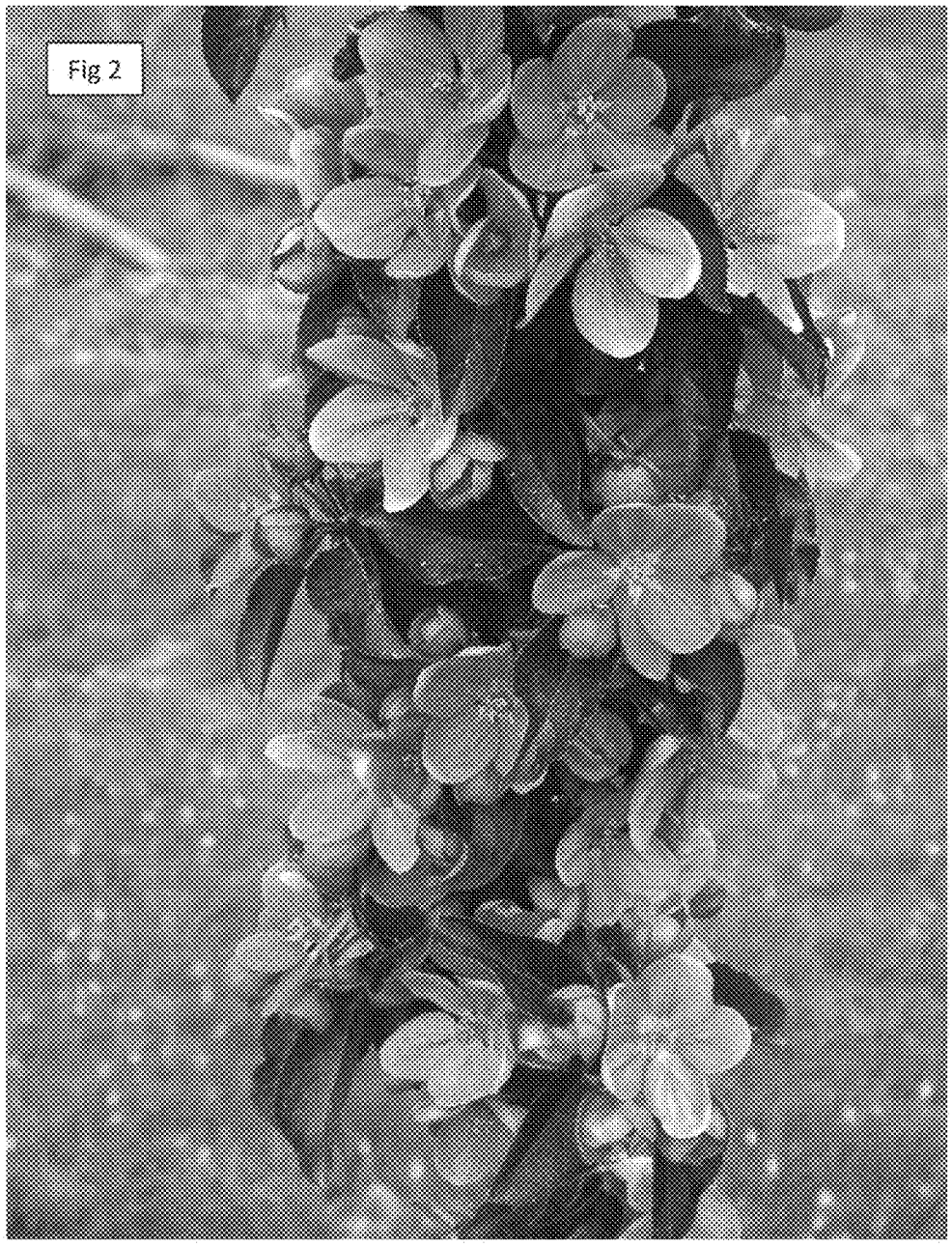
FIG. 2 is a section of a tree of the new variety with opening and fully opened flowers.
Figure 3:
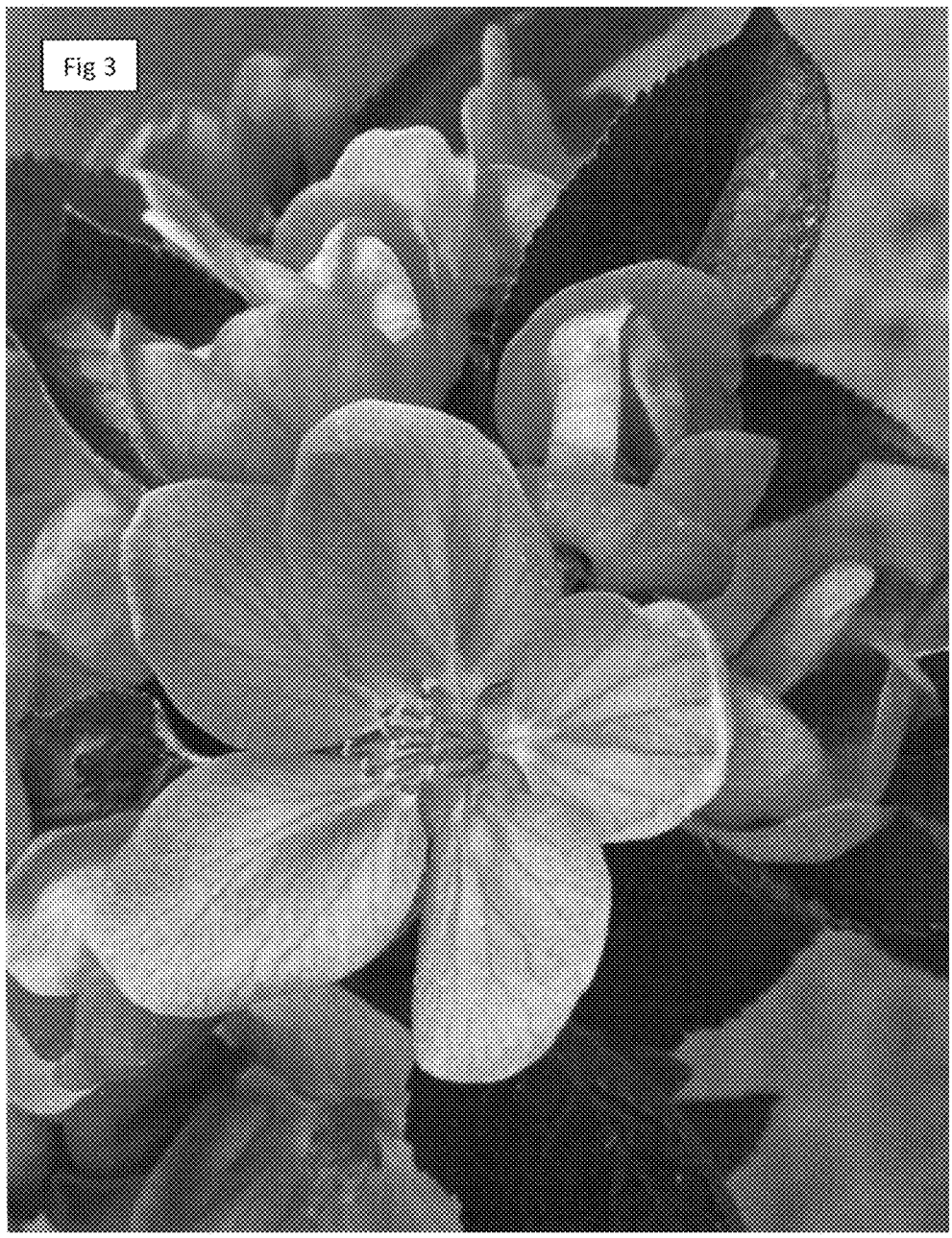
FIG. 3 shows a close-up view of the blossoms of the new variety.
Figure 4:
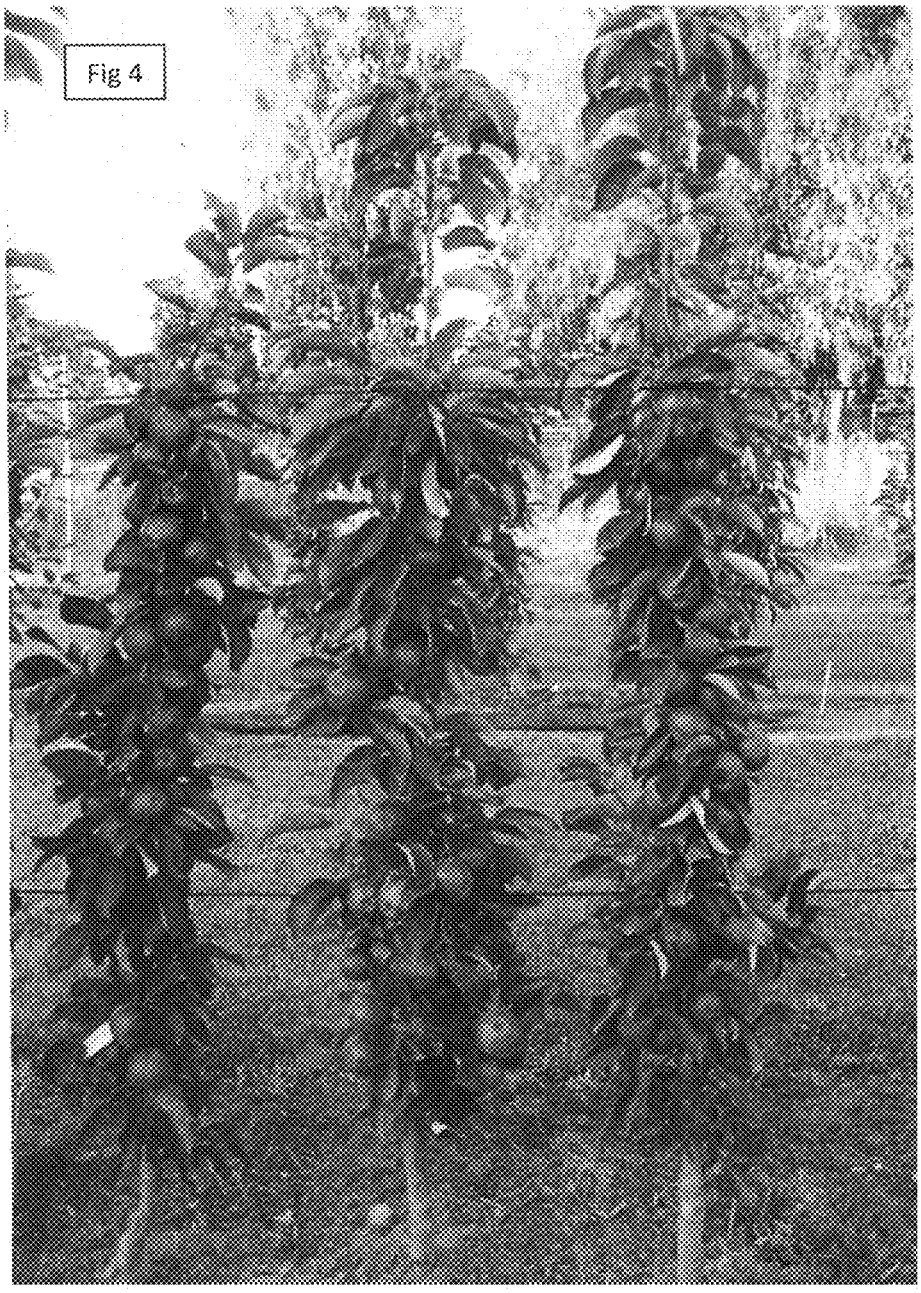
FIG. 4 shows trees of the new variety grafted on MM 26 rootstock with the fruits at picking maturity.
Figure 5:
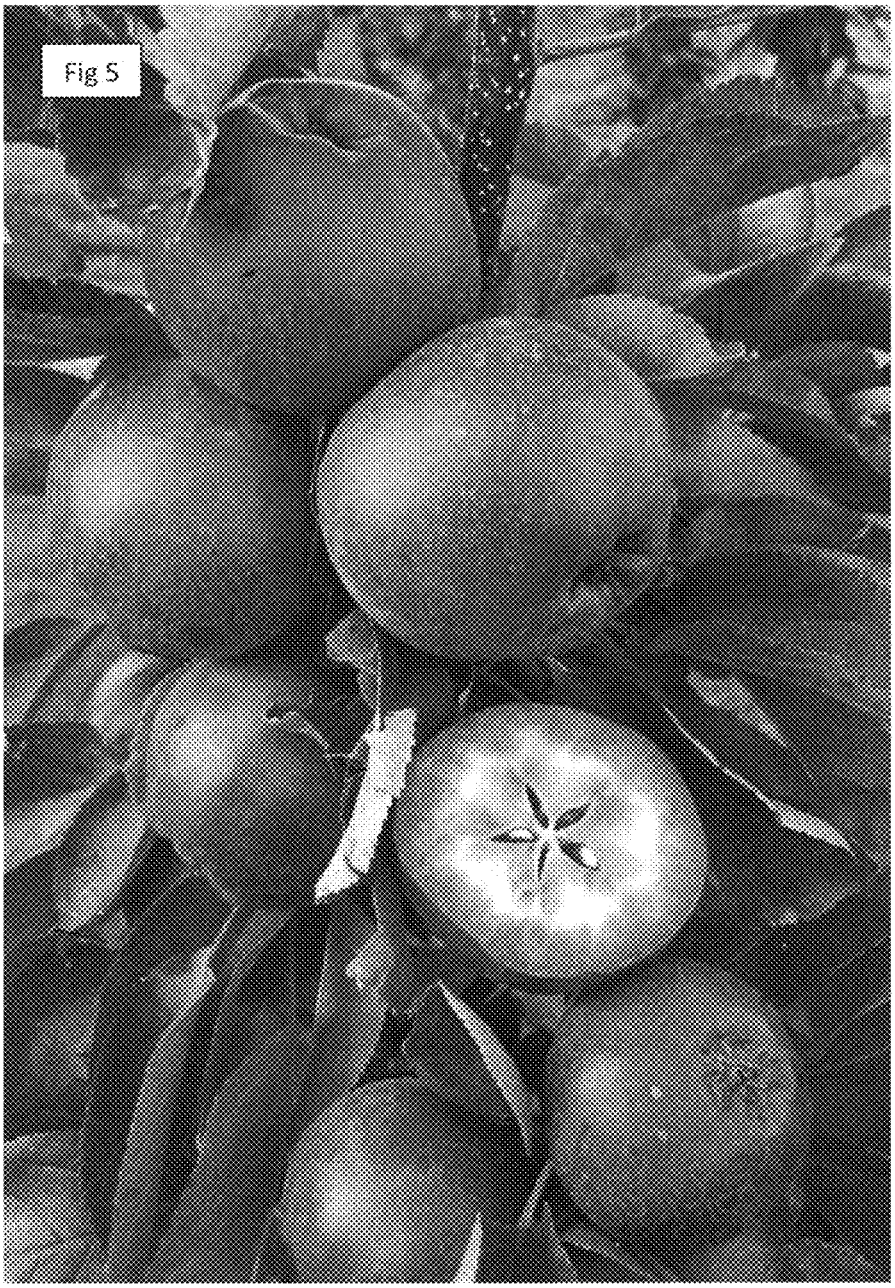
FIG. 5 is a close-up view of the fruits and the fruit flesh of the new variety at picking maturity.

The following detailed description sets forth the characteristics of the new cultivar. The new variety was grown under natural field conditions in The Czech Republic. The growing area is 310 m above sea level with a mean annual temperature of 7.7° C. and a mean annual precipitation of 680 mm. The following fertilizer combination was used (Kg/ha/year): 55 parts nitrogen, 25 parts phosphorous, 60 parts potassium, 55 parts calcium, and 5 parts magnesium. Color references are primarily to The R.H.S. Colour Chart of The Royal Horticultural Society of London and were identified under natural light.

TREE

Age: 6 years from the year of budding on seedling rootstock.
Size: 2.8 m high, 0.4 m wide.
Vigor: Average.
Density: Thick.
Form: Erect and compact; substantially free of side branches.
Production: Very precocious, but not measured due to the ornamental nature of 'ROSALIE'.
Growth type: Columnar.
Bearing: Mainly on spurs.
Trunk:
- *Size*.—Approximately 5.5 cm in diameter at 30 cm from the soil line.
- *Surface texture*.—Smooth to slightly rough.
- *Bark color*.—200B.
- *Lenticels* (50 *cm above ground*).—Length: 2 mm to 5 mm. Width: 1 mm. Color: 165C. Density: Approximately 5 to 7 lenticels per 1 $cm^2$.

Branches:
- *Overall description*.—A conventional branching system along the tree trunk is lacking.
- *Surface texture*.—Smooth to slightly rough.
- *Color*.—Between 200A to 200B.
- *Form*.—Straight.
- *Average crotch angle*.—About 30 degrees.
- *Bud arrangement*.—Alternate at intervals from 1.5 cm to 2.5 cm.
- *Lenticels*.—Length: 0.5 mm to 1.0 mm. Width: 0.5 mm. Shape: Round to oval. Density: Dense, with 8 to 12 lenticels per 1 $cm^2$. Color: 161C.

Leaves:
- *Length*.—About 90 mm to about 106 mm, averaging 99 mm.
- *Width*.—About 65 mm to about 80 mm, averaging about 74 mm.
- *Form*.—Rounded to oval.
- *Texture*.—Smooth.
- *Thickness*.—Moderately thick.
- *Base*.—Predominantly symmetric.
- *Apex*.—Acute; mostly straight.
- *Margin*.—Biserrate.
- *Pubescence*.—Upper surface: None present. Lower surface: Very little.
- *Color*.—Young leaves: Upper surface: 187A. Lower surface: 187B. Mature leaves: Upper surface: 139A. Lower surface: 146B.
- *Veins*.—Venation type: Net-like, medium dense. Color: Upper surface: 187B. Lower surface: 187D.
- *Petiole*.—Shape: Straight with thickening at the base. Length: About 25 mm to about 49 mm, averaging about 35 mm. Diameter: About 2.0 mm to 3.0 mm in the middle. Color: 187A to 187B.
- *Stipules*.—Average number per leaf: 2. Length: 6 mm to 8 mm. Width: 0.85 mm. Color (both surfaces): Similar to the color of the leaves through maturity.

Flower buds:
- *Pedicel*.—Length: Typically in the range of 16 to 20 mm, with an average of about 20 mm. Diameter: 13 mm on average. Color: Predominantly 184A.
- *Bud*.—Length: 17.5 mm on average. Width: 14 mm on average. Shape: Acuminate. Color: 60B.

Flowers:
- *Bloom timing*.—Medium; about 2 days before 'Golden Delicious'.
- *Blooming period*.—Medium; approximately 10 days.
- *Pollination requirements*.—Self-sterile, needs pollinators.
- *Number of flowers per cluster*.—6.
- *Fragrance*.—Faint.
- *Petals*.—Number: 5. Length: 28 mm on average +/−2 mm. Width: 20 mm on average +/−2 mm. Shape: Ovate. Aspect: Positioned overlapping. Apex: Oval. Base: Acuminate. Margin: Entire. Texture and appearance: Soft and smooth. Color: When opening: Upper surface: 63A. Lower surface: 63B. Fully opened: Upper surface: 63B. Lower surface: 63B to 63C.
- *Sepals*.—Number per flower: 5. Shape: Elongated and conical; pointed. Apex: Long and conical; pointed. Margin: Entire. Texture: Fine pubescence present. Length: 7 mm to 9 mm from the union. Width: 4 mm to 5 mm at the base, 3 mm in the middle. Color: Upper surface: 144B with an apex of 59A. Lower surface: 59B in the middle with an apex of 59A.
- *Stamens*.—Number (per flower): 19 to 20. Filament length: 6 mm to 9 mm.
- *Anthers*.—Shape: Oval. Length: 2 mm to 3 mm. Color: 24D.
- *Pollen*.—Color: 12B. Amount (generally): Medium to high.
- *Pistils*.—Length: 12 mm on average.
- *Style*.—Length: 7 mm to 8 mm on average. Color: 54C.
- *Stigma*.—Shape: Rounded. Color: 51D.

Fruit:
- *Maturity when described*.—After 1 month from picking and in common storage.
- *Date of picking*.—Oct. 20, 2011.
- *Average weight*.—61 g.
- *Size*.—Axial diameter: About 50 mm. Transverse diameter: About 55 mm.
- *Form*.—Broadly globose-conical.
- *Cavity*.—Shape: Funnel-shaped and free of russet. Depth: Average of 13 mm. Breadth: Average of 55 mm.
- *Basin*.—Shape: Saucer-shaped. Depth: Average of 5 mm. Width: Average of 20 mm.
- *Calyx*.—Persistent with erect lobes.

Skin:
- *Thickness*.—Medium.
- *Texture*.—Smooth, free of russet.
- *Tendency to crack*.—Absent.
- *Color*.—46C to 53A.
- *Ground color*.—153D is the closest.

Flesh:

*Aroma*.—Weak, like an ornamental apple.

*Color*.—Partly 51A and partly 158D.

*Texture*.—Fine grained and soft.

*Eating quality*.—Not applicable.

Locules:

*Average number per fruit*.—5.

*Length*.—8.8 mm to 10.6 mm.

*Width*.—3.8 mm to 5.6 mm.

*Form*.—Typical for apples.

Core:

*Bundle area*.—On longitudinal section — onion-shaped; on cross-section — core locules are closed or slightly open. The core line height is 11 mm and width is 21 mm.

*Bundle*.—Vascular strands weakly distinct and almost invisible.

*Calyx tube*.—Short.

*Styles*.—Persistent as dry residues, closed with calyx lobes.

*Stamens*.—Persistent as dry residues, closed with calyx lobes.

*Seed cells*.—Wall: Smooth. Depth: 12 mm. Breadth: 5 mm at cross-section. Longitudinal section: About 13 mm (length of seed cell).

Seeds:

*Number perfect*.—8.

*Number in one cell*.—1 to 2.

*Length*.—10 mm.

*Breadth*.—5 mm.

*Form*.—Flattened and pyramidal with an acute tip.

*Color*.—177A.

Stem:

*Length*.—Average of 20 mm.

*Width*.—1.5 mm to 2 mm.

*Color*.—59A.

Use: As an ornamental variety.

Shipping quality: Not tested.

Keeping quality: Not tested.

Tree winter hardiness: No frost damage observed at the place of origin, lowest winter temperatures approximately −20° C.

Bud winter hardiness: No frost damage observed at the place of origin, lowest winter temperatures approximately −20° C.

Drought tolerance: Not tested.

Disease resistance: $V_f$-resistance against scab; mildew tolerance observed.

Pest resistance/susceptibility: No sensitivities observed.

Multiplication ability:

*Layering*.—Not applicable, multiplication is only by budding/grafting.

*Hardwood cuttings*.—On vegetatively propagated rootstocks.

We claim:

1. A new and distinct variety of *Malus domestica* (Borkh.) apple tree substantially as is herein described and illustrated.

* * * * *